US00PP21914P2

(12) United States Plant Patent
Horvath

(10) Patent No.: US PP21,914 P2
(45) Date of Patent: May 10, 2011

(54) ***LEUCANTHEMUM SUPERBUM* PLANT NAMED 'DAISY DUKE'**

(50) Latin Name: *Leucanthemum superbum*
Varietal Denomination: Daisy Duke

(76) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 12/589,810

(22) Filed: Oct. 29, 2009

(51) Int. Cl.
*A01H 5/00* (2006.01)
(52) U.S. Cl. ..... Plt./285
(58) Field of Classification Search ..... Plt./285
See application file for complete search history.

*Primary Examiner* — Kent L Bell

(57) ABSTRACT

A new and distinct variety of *Leucanthemum superbum* plant as shown and described, characterized by single white inflorescences that overlap and touch, a dome shaped habit, a medium height and a uniform growth habit.

2 Drawing Sheets

Latin name: *Leucanthemum superbum.*
Cultivar name: 'Daisy Duke'.

BACKGROUND OF THE INVENTION

The present invention relates to a new and distinct plant of *Leucanthemum superbum* plant named 'Daisy Duke' characterized by single white inflorescences that overlap and touch, a dome shaped habit, a medium height and a uniform growth habit.

The new *Leucanthemum* was raised as an open pollinated seedling from seed sown as *Leucanthemum superbum* 'Hebron Hardy', not patented, at a nursery in Hebron, Ill. in 2005. The selection of the new plant was due to its single white inflorescences that overlap and touch, a dome shaped habit, and a medium height.

Asexual division, and cutting propagation have been the means of reproduction. Propagation has taken place at a nursery in Hebron, Ill. since 2006. The new *Leucanthemum* has shown to be stable and identical in reproduction after rooting over 2000 plants from 2006 to 2009.

SUMMARY OF THE INVENTION

The new *Leucanthemum superbum* plant named 'Daisy Duke' characterized by single white inflorescences that overlap and touch, a dome shaped habit, a medium height and a uniform growth habit have been observed to be unique and stable.

Plants of the new *Leucanthemum* can be compared to plants of *Leucanthemum superbum* 'Becky' not patented.

1. The new *Leucanthemum* plant has a mature size measuring 45-60 cm high and 50-60 cm wide while *Leucanthemum superbum* 'Becky' measures 100-120 cm high and over 100 cm wide.
2. The new *Leucanthemum* plant has a dome shaped habit while *Leucanthemum superbum* 'Becky' has an open habit.
3. The new *Leucanthemum* plant has green colored stems at the base of the plant while *Leucanthemum superbum* 'Becky' has red colored stems at the base of the plant.
4. The new *Leucanthemum* plant has smaller foliage approximately 25 mm wide while *Leucanthemum superbum* 'Becky' has foliage that reaches approximately 35 mm wide.

Plants of the new *Leucanthemum* can also be compared to the seed parent plant *Leucanthemum superbum* 'Hebron Hardy', not patented.

1. The new plant has a uniform height since it is produced asexually from vegetative division and cutting propagation while the seed parent is produced from seed and the height varies.

Plants of the new *Leucanthemum* can also be compared to plants of *Leucanthemum superbum* 'Leumayel', patented.

1. The new plant inflorescence color is white while the inflorescence color of the *Leucanthemum superbum* 'Leumayel' plant is yellow.

DESCRIPTION OF PHOTOGRAPHS

Figure 1:
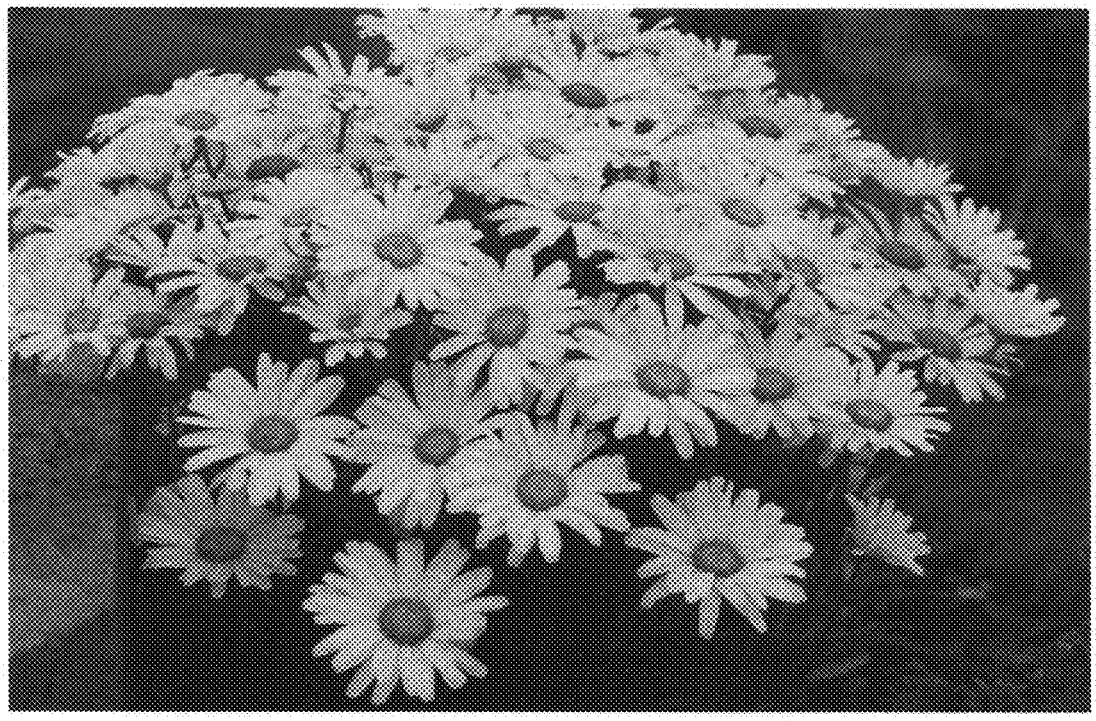
Figure 2:
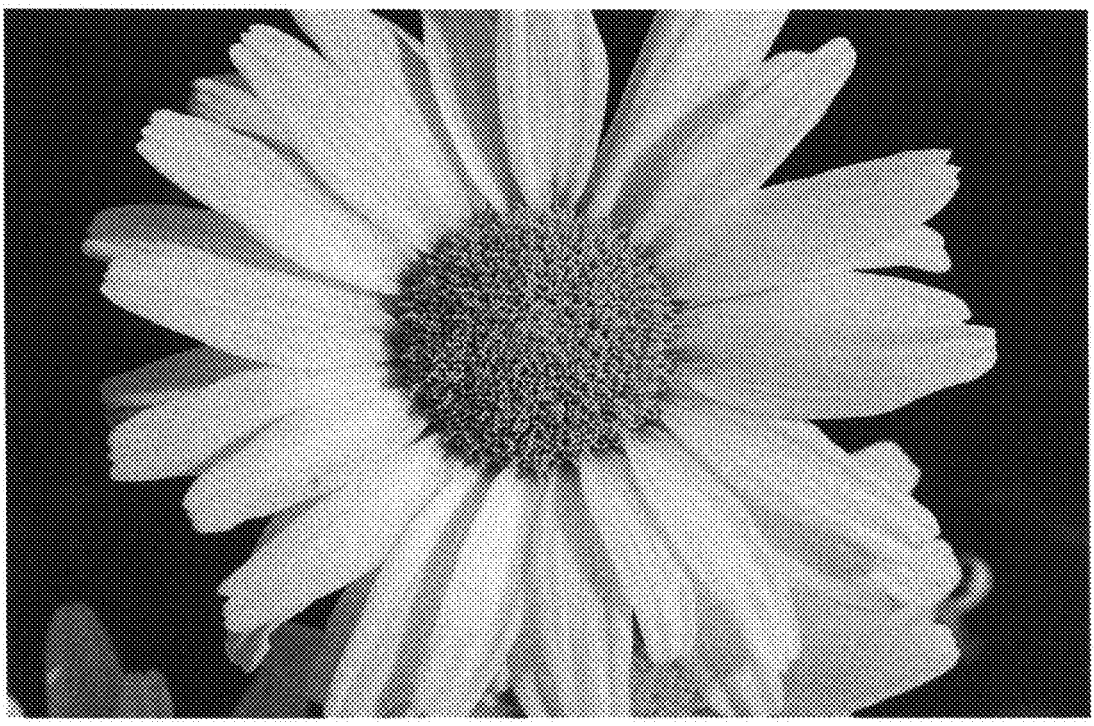
Figure 3:
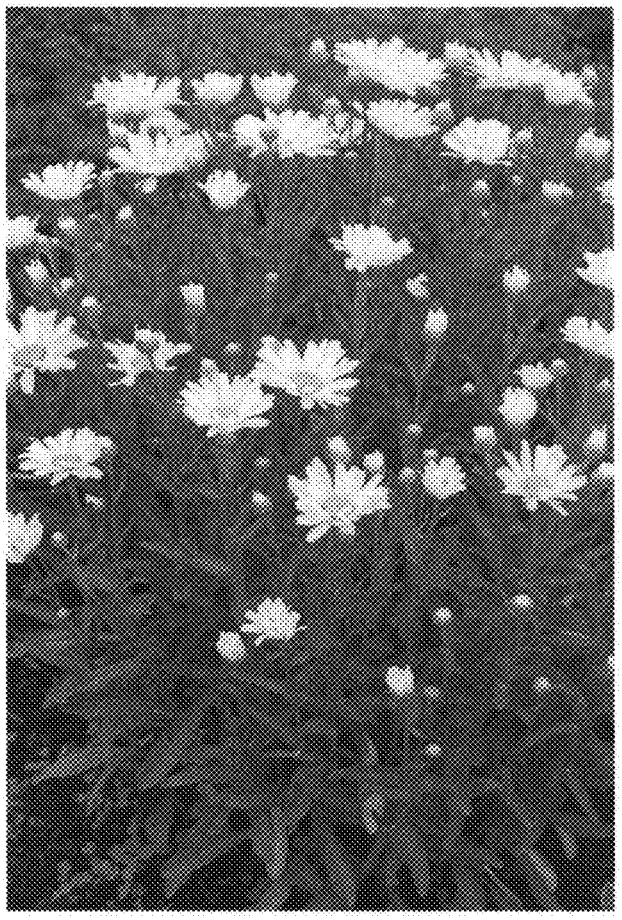
Figure 4:
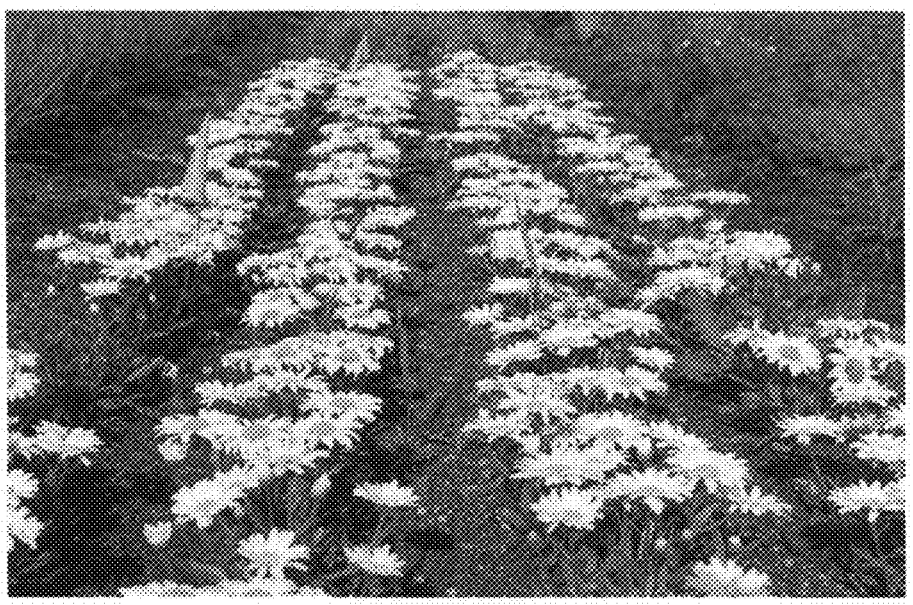

FIG. 1. A blooming 2 year old plant in July.
FIG. 2. A close up of a single inflorescence.
FIG. 3. A budding 3 year old plant in June.
FIG. 4. A first year planting showing uniformity.

DETAILED BOTANICAL DESCRIPTION

In the following description, color references are made to The Royal Horticultural Society Colour Chart. Plants used for the description were grown for two seasons at a nursery in Hebron, Ill. Measurements and numerical values represent averages of typical plants.

Botanical classification: *Leucanthemum superbum* cultivar Daisy Duke.

Parentage: Male or pollen parent an unknown *Leucanthemum superbum,* female or seed parent *Leucanthemun superbum* 'Hebron Hardy'.

Propagation: Vegetative division and cutting propagation.

Plant description: Overall habit of the new *Leucanthemum* is a dome shaped clump, with stems topped by white inflorescences that overlap and touch starting in mid to late June.

*Plant height.*—45-60 cm.
*Plant width.*—50-60 cm.
*Primary stem diameter.*—6-8 mm.
*Primary and secondary stem description.*—Branching, with 20 or more leaves. Leaves get smaller as they go up the stem.
*Primary and lateral stem texture.*—Sparsely pubescent with hairs up to 2 mm long.

*Secondary stem description.*—Average 3 lateral stems per primary stem.
*Secondary stem length.*—20 cm.
*Secondary stem diameter.*—3-4 mm.
*Secondary stem internodes.*—2-6 cm.

Foliage:
*Type.*—Deciduous.
*Leaf arrangement.*—Alternate.
*Length.*—9-12 cm.
*Width.*—25 mm.
*Shape.*—Spatulate.
*Apex.*—Acute.
*Base.*—Cuneate.
*Margin.*—Dentate.
*Texture.*—Smooth, glabrous, moderately glossy.
*Adaxial leaf description.*—Color is 139 A.
*Abaxial leaf description.*—Color is 138 C.

Bud:
*Bud shape.*—Flattened globular.
*Bud length.*—8-9 mm.
*Bud diameter.*—13-15 mm.
*Bud color.*—137 C.

Inflorescence:
*Inflorescence type.*—Composite on basal flowering stems.
*Position.*—Terminal.
*Number of inflorescences per plant.*—Approximately 50 or more.
*Arrangement.*—Disc and ray florets.
*Disc floret.*—Four fused petals, yellow color 12 A.
*Disc floret diameter.*—2-3 mm at apex, 1-2 mm at base.
*Disc floret shape.*—Rotate.
*Disc floret length.*—3-5 mm.
*Disc floret width.*—1 mm.
*Disc floret apex.*—Acute.
*Disc floret margin.*—Entire.
*Disc floret count.*—Approximately 200 per inflorescence.
*Ray floret size.*—4 cm length and 8 mm width.
*Ray floret color.*—Both Adaxial and Abaxial surfaces are close to 155 A and 155 B.
*Ray floret aspect.*—Upright.
*Ray floret shape.*—Oblanceolate.
*Ray floret apex.*—Tridentate.
*Ray floret base.*—Cuneate.
*Ray floret margin.*—Entire.
*Ray floret count.*—Approximately 30 per inflorescence.
*Ray floret texture.*—Both the upper and lower surfaces are smooth, glabrous.
*Overall inflorescence size.*—9-10 cm or more across in diameter with ray florets.
*Bloom period and duration.*—Late June through July.
*Blooming habit.*—Domed, terminal on up to 45-60 cm stems.
*Scent.*—No scent noticed.
*Fruit.*—None observed.

Disease resistance: Resistance to diseases common to *Leucanthemum* has not been observed on plants grown under nursery conditions.

Hardiness: Plants of the new *Leucanthemum* have been observed to be hardy to USDA Zone 5.

I claim:

1. A new and distinct variety of *Leucanthemum superbum* plant as shown and described, characterized by single white inflorescences that overlap and touch, a dome shaped habit, a medium height and a uniform growth habit.

* * * * *